(12) United States Patent
Quin

(10) Patent No.: US 9,855,335 B2
(45) Date of Patent: Jan. 2, 2018

(54) TIGECYCLINE COMPOSITION FOR INJECTION

(71) Applicant: Galenicum Health S.L., Barcelona (ES)

(72) Inventor: Jihong Quin, Shanghai (CN)

(73) Assignee: GALENICUM HEALTH S.L., Barcelona (ES)

( * ) Notice: Subject to any disclaimer, the term of this patent is extended or adjusted under 35 U.S.C. 154(b) by 0 days.

(21) Appl. No.: 14/413,854

(22) PCT Filed: Apr. 7, 2013

(86) PCT No.: PCT/CN2013/000397
§ 371 (c)(1),
(2) Date: Jan. 9, 2015

(87) PCT Pub. No.: WO2013/139179
PCT Pub. Date: Sep. 26, 2013

(65) Prior Publication Data
US 2015/0190511 A1    Jul. 9, 2015

(30) Foreign Application Priority Data

Mar. 22, 2012  (CN) .......................... 2012 1 0078509

(51) Int. Cl.
| | |
|---|---|
| A61K 9/19 | (2006.01) |
| A61K 9/00 | (2006.01) |
| A61K 31/65 | (2006.01) |
| A61K 47/02 | (2006.01) |
| A61K 47/18 | (2017.01) |

(52) U.S. Cl.
CPC .......... *A61K 47/183* (2013.01); *A61K 9/0019* (2013.01); *A61K 9/19* (2013.01); *A61K 31/65* (2013.01); *A61K 47/02* (2013.01)

(58) Field of Classification Search
CPC ............ A61K 9/19; A61K 9/00; A61K 31/65; A61K 47/02; A61K 47/183; A61K 47/18
See application file for complete search history.

(56) References Cited

U.S. PATENT DOCUMENTS

| | | | |
|---|---|---|---|
| 2009/0275660 A1 | 11/2009 | Chauhan et al. | |
| 2014/0323443 A1 | 10/2014 | Uchil et al. | |

FOREIGN PATENT DOCUMENTS

| | | | |
|---|---|---|---|
| CN | 101132775 | | 2/2008 |
| CN | 101152152 | | 4/2008 |
| CN | 101401812 | | 4/2009 |
| CN | 101919816 | * | 12/2010 |
| CN | 101919816 A | | 12/2010 |
| CN | 102138925 | | 8/2011 |

OTHER PUBLICATIONS

CN101919816—translation, translation of CN 101919816, 2010.*
Arginine, 2016, http://www.differencebetween.com/difference-between-arginine-and-vs-l-arginine/.*
International Search Report for International Application No. PCT/CN2013/000397 dated Jul. 18, 2013 (3 pages).

* cited by examiner

*Primary Examiner* — Sun Jae Yoo
(74) *Attorney, Agent, or Firm* — Daniel R. Evans

(57) ABSTRACT

Disclosed is a tigecycline composition for injection, comprising the active component, tigecycline, and a propping agent. Also included is a stabilization agent. Also disclosed is a stable, pharmaceutically acceptable reconstitution liquid having freeze-dried tigecycline. The tigecycline composition for injection of the present invention has good redissolution, and can dissolve without intense shaking, thereby avoiding foams caused by intense shaking. Upon testing, the tigecycline composition and the tigecycline composition-diluted reconstitution liquid prepared in the present invention prove to have substantially lowered oxidation degradation and epimer generation and increased stability of the tigecycline preparation. Compared to the compositions currently in clinical use, the composition of the present invention can increase the treatment effect of tigecycline, avoid safety risks caused by lactose, is easy to produce and store, and has a clinical usage stability, satisfying the requirements for clinical medicine.

21 Claims, No Drawings

# TIGECYCLINE COMPOSITION FOR INJECTION

This application is a National Stage Application of PCT/CN2013/000397, filed on Apr. 7, 2013, which claims benefit of Chinese Application No. 201210078509.9, filed on Mar. 22, 2012, the subject matter of which is incorporated herein by reference. The present application claims priority to the above-noted applications.

TECHNICAL FIELD

The invention belongs to the technical field of pharmaceutical preparations, and particularly relates to a stable tigecycline composition for injection.

BACKGROUND ART

Drug-resistant bacteria, particularly methicillin-resistant *Staphylococcus aureus* (MRSA) infection, is violently spreading in the seven main global medical market areas. In America, community-acquired MRSA infection is on the rise. According to recent research data, 9% of patients with infectious diseases in UK National Health Service (NHS) hospitals acquired the infection through surgical operations or outpatient services; about 100,000 people suffer from the invasion of the infection every year, and about 5,000 people die, and moreover, it can cause the expenditure of more than 1 billion pounds. Thus the seriousness of the MRSA infection is evident.

Tigecycline is the first glycylcycline antibiotic approved for clinical intravenous administration, similar to tetracyclines in structure, and was developed by Wyeth and is on the market. Glycylcycline antibiotic preparations are derivatives of minocycline. The mechanism of action of tetracyclines is that tetracyclines bind to the A site of the 30S ribosome to prevent amino acid charged transfer RNA from entering the ribosome, thereby blocking the formation of peptide chains with amino acid residues. Glycylcyclines are similar to the tetracyclines in their mechanism of action, but have higher affinity than the latter. Glycylcyclines directly interact with another area of the A site of the ribosome. Tigecycline inhibits the formation of the peptide chains and influences the structural formation of bacteria and the realization of certain functions so as to kill the bacteria or inhibit bacterial reproduction.

Research shows that tigecycline can be used for adult intra-abdominal infections (cIAI) and complicated skin and soft tissue infections (cSSSI) caused by *Escherichia coli*, *Enterococcus faecalis* (only vancomycin-susceptible strains), *Staphylococcus aureus* (methicillin-susceptible and resistant strains), *Streptococcus agalactiae*, *Streptococcus anginosus* genus (including *Streptococcus anginosus*, *Streptococcus anginosus intermedius*, and *Streptococcus constellatus*), *Streptococcus pyogenes* and *Bacteroides fragilis*, *Citrobacter freundii*, *Aerobacter cloacae*, *Escherichia coli*, *Klebsiella oxytoca*, *Klebsiella pneumonia*, *Enterococcus faecalis* (only vancomycin-susceptible strains), *Staphylococcus aureus* (only methicillin-susceptible strains), *Bacteroides thetaiotaomicron*, *Bacteroides uniformis*, *Clostridium perfringens*, *Peptostreptococcus micros* and the like. Tigecycline has the characteristic that the antibacterial spectrum is broad.

In addition, research also shows that tigecycline can overcome two main drug-resistance mechanisms, efflux pump and ribosome protection, which have limited the use of many antibiotics. Therefore, tigecycline does not develop drug-resistance easily, and will be applicable in a very broad range.

Tigecycline is not stable enough in solution, and is easily subjected to breakage due to oxidation degradation and epimerization, and the breakage can be accelerated by heating; a common solution is that tigecycline is prepared into a freeze-dried powder for injection; however, we found that even if tigecycline is prepared into a freeze-dried preparation, the stability of tigecycline during preparation, transportation and storage cannot be guaranteed, related substances in the preparation are still significantly increased, moreover, the requirements for the formulation and infusion time in clinical use are stringent, and thus this will be very inconvenient and hidden danger will be brought to the safety of patients taking the medication.

CN 101132775 A discloses a freeze-dried powder for injection consisting of tigecycline and a suitable carbohydrate. The occurrence of oxidation and epimerization in the powder for injection is also effectively inhibited by the formulation. The suitable carbohydrate disclosed by Wyeth is lactose, and was validated by the FDA and approved to appear on the market. However, according to the lactose standards in the 2010 version of China Pharmacopeia, lactose can only be used as an excipient of an oral preparation. Lactose is not used as the injection excipient in any National Formulary in the world at present, potential safety hazards may be brought about by using lactose as the excipient for injection, and moreover, the proportion of lactose intolerance of Asian people is higher, and adverse effects caused by lactose intolerance may be increased.

In order to broaden the applicable range of people and lower the clinical use risk, and increase the stability of tigecycline at the same time, the invention provides a novel tigecycline composition for injection.

SUMMARY OF THE INVENTION

A purpose of the invention is providing a stable tigecycline composition for injection.

Another purpose of the invention is providing a stable and pharmaceutically acceptable reconstituted solution of freeze-dried tigecycline.

The invention provides a tigecycline composition for injection, comprising an active component, tigecycline, and a propping agent.

The tigecycline composition for injection also comprises a stabilizing agent.

The weight ratio among components of the tigecycline composition for injection is: tigecycline 1.0, the propping agent 0.2-10, and the stabilizing agent 0-4, preferably tigecycline 1.0, the propping agent 0.3-4, and the stabilizing agent 0-2.

The pH value of the tigecycline composition for injection is 3.0-8.0. Preferably the pH value is 4.0-6.0.

The amount of tigecycline in the composition is 50 mg.

The propping agent therein is selected from one or several of L-arginine, L-arginine hydrochloride, D-arginine, DL-arginine, and a salt formed by L, D or DL-arginine with an acid or alkali, preferably L-arginine hydrochloride.

The stabilizing agent therein is selected from one of sodium chloride, hydrochloric acid and sodium hydroxide or a mixture of hydrochloric acid and sodium hydroxide, preferably sodium chloride.

In one preferred embodiment of the invention, the propping agent is L-arginine hydrochloride, and the stabilizing agent is sodium chloride.`

The tigecycline composition for injection of the invention is a solution for injection or a solid preparation for injection, preferably a solid preparation for injection, such as a freeze-dried powder for injection.

A stable and pharmaceutically acceptable reconstituted solution of freeze-dried tigecycline of the invention is prepared by treating the freeze-dried powder of the tigecycline composition for injection with a suitable amount of a pharmaceutically acceptable diluent.

The diluent is normal saline, 5% glucose solution or lactated Ringer's solution, and the formed reconstituted solution has good stability.

The tigecycline composition for injection of the invention has good redissolution, and can dissolve without vigorous shaking. Therefore, foams caused by vigorous shaking can be avoided.

The experiments demonstrated that the tigecycline composition for injection and the reconstituted solution formed by diluting the tigecycline composition for injection of the invention had significantly lowered the oxidation degradation and epimer generation, and enhanced the stability of a tigecycline preparation. Compared with existing compositions for clinical use, the composition of the invention can avoid potential safety hazards which may be caused by lactose, has stability during production, storage and clinical use, and meets the requirements of clinical medications.

PARTICULAR EMBODIMENTS

Methods described below are exemplary, and are not meant to limit the invention.

Firstly, the propping agent is dissolved in water cooled to room temperature after being boiled; secondly, tigecycline is added and stirred until the tigecycline is fully dissolved, and then adjusted to a corresponding pH value using an acid or alkali; and finally, the solution is freeze-dried, and charged with nitrogen, capped with a rubber stopper and a seal. During the preparation, activated carbon for injection is added as required, stirred, roughly filtered, decarbonized, filtered with a micropore filtration membrane, and sterilized.

The solution of the composition of the invention can be freeze-dried in a tubular vial and made into the form of a single-dose administration. When needed, a desired amount of a diluent can be added for reconstitution, and a totally dissolved reconstituted solution will be formed in a short time by gently shaking.

Compositions in each embodiment below are freeze-dried once in the same freeze dryer, and put in the same drying oven, and the raw materials used are from the same batch. Numeric ratios in brackets in the following examples are weight ratios.

EXAMPLE 1

Formulation I: water+tigecycline, pH 4.5

500 mg of tigecycline was weighed, and dissolved in 20 ml of deoxidized water (pure water cooled after being boiled, the same as below), the pH was adjusted to 4.5 with 1 mol/l HCl, and then the solution was distributed into 10 vials of 10 ml, with 2 ml per vial.

Formulation II: lactose+tigecycline (2:1), pH 4.5 (the advantageous formulation of patent CN 101132775 A)

1000 mg of lactose was weighed and dissolved in 20 ml of deoxidized water, 500 mg of tigecycline was added, and shaken for dissolution, the pH was adjusted to 4.5 with 1 mol/l HCl, and then the solution was distributed into 10 vials of 10 ml, with 2 ml per vial.

Formulation III: mannitol+Vitamin C+tigecycline (4:0.3:1), pH 4.5

2000 mg of mannitol was weighed and dissolved in 20 ml of deoxidized water, and after 150 mg of Vitamin C was added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation IV: mannitol+Vitamin C+glycerol+tigecycline (4:0.3:0.25:1), pH 4.5

2000 mg of mannitol was weighed and dissolved in 20 ml of deoxidized water, and after 150 mg of Vitamin C and 125 mg of glycerol were added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation V: mannitol+Vitamin C+tigecycline (4:0.3:1), pH 8.0

2000 mg of mannitol was weighed and dissolved in 20 ml of deoxidized water, and after 150 mg of Vitamin C was added and dissolved, 500 mg of tigecycline was added and shaken for dissolution, the pH was adjusted to 8.0 with 1 mol/l NaOH, and then the solution was distributed into 10 vials of 10 ml, with 2 ml per vial.

Formulation VI: mannitol+Vitamin C+Tween 80+tigecycline (4:0.3:0.25:1), pH 4.5

2000 mg of mannitol was weighed and dissolved in 20 ml of deoxidized water, and after 150 mg of Vitamin C and 125 mg of Tween 80 were added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation VII: saccharose+tigecycline (2:1), pH 4.5

1000 mg of saccharose was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation VIII: saccharose+glycerol+tigecycline (2:0.15:1), pH 4.5

1000 mg of saccharose was weighed and dissolved in 20 ml of deoxidized water, and after 75 mg of glycerol was added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation IX: mannitol+calcium chloride+tigecycline (4:0.4:1), pH 4.5

2000 mg of mannitol was weighed and dissolved in 20 ml of deoxidized water, and after 200 mg of calcium chloride was added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation X: mannitol+sodium chloride+tigecycline (4:0.4:1), pH 4.5

2000 mg of mannitol was weighed and dissolved in 20 ml of deoxidized water, and after 200 mg of sodium chloride was added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation XI: mannitol+tigecycline (4:1), pH 4.5

2000 mg of mannitol was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation XII: L-arginine+tigecycline (0.5:1), pH 8

250 mg of L-arginine was weighed and dissolved in 20 ml of deoxidized water, 500 mg of tigecycline was added and shaken for dissolution, the pH was adjusted to 8.0 with 1 mol/l HCl, and then the solution was distributed into 10 vials of 10 ml, with 2 ml per vial.

All the vials holding sample solutions were placed in the freeze dryer for freeze drying, and after freeze drying, the vials were charged with nitrogen, with compacted plugs and pressed caps. Moisture and purity were determined on day 0, then the remaining samples were placed in the drying oven at 60° C., and the purity was determined on day 5 and day 10. Experiment results are shown in Table 1 (data in the table is arranged from high to low for the purity on day 10 at 60° C.).

lations X and XI after 10 days at 60° C., the stability of the tigecycline can be increased where sodium chloride is added; although the color of the sample of formulation XII has changed after 10 days at 60° C., this formulation is only inferior to the lactose formulation in the stability of tigecycline.

EXAMPLE 2

Formulation I: water+tigecycline, pH 8.0

500 mg of tigecycline was weighed, dissolved in 20 ml of deoxidized water, the pH was adjusted to 8.0 with 1 mol/l NaOH, and then the solution was distributed into 10 vials of 10 ml, with 2 ml per vial.

Formulation II: sodium sulfite+tigecycline (0.2:1), pH 8.0

100 mg of anhydrous sodium sulfite was weighed and dissolved in 20 ml of deoxidized water, 500 mg of tigecycline was added and shaken for dissolution, the pH was

TABLE 1

| Formulation number | Formulation name (weight ratio) | Purity at 60° C. on day 0 | Purity At 60° C. on day 5 | Purity At 60° C. on day 10 | Moisture % | Notes |
|---|---|---|---|---|---|---|
| Formulation II | Lactose + tigecycline (2:1), pH 4.5 | 99.58% | 98.76% | 97.71% | 1.87% | |
| Formulation XII | L-arginine + tigecycline (0.5:1), pH 8.0 | 99.50% | 97.89% | 95.04% | 2.04% | The sample color has turned from orange yellow into grayish yellow after 10 days |
| Formulation VII | Saccharose + tigecycline (2:1), pH 4.5 | 99.71% | 90.85% | 91.81% | 3.29% | |
| Formulation I | Water + tigecycline, pH 4.5 | 99.63% | 94.67% | 89.72% | 3.67% | |
| Formulation X | Mannitol + sodium chloride + tigecycline (4:0.4:1), pH 4.5 | 99.84% | 93.09% | 87.53% | 0.89% | |
| Formulation XI | Mannitol + tigecycline (4:1), pH 4.5 | 99.68% | 91.34% | 83.53% | 0.94% | |
| Formulation V | Mannitol + Vitamin C + tigecycline (4:0.3:1), pH 8.0 | 99.01% | 87.50% | 79.01% | 0.95% | The sample color has turned from orange yellow into grayish yellow after 10 days |
| Formulation III | Mannitol + Vit C + tigecycline (4:0.3:1), pH 4.5 | 98.79% | 79.63% | 72.82% | 1.96% | |
| Formulation VI | Mannitol + Vit C + Tween 80 + tigecycline (4:0.3:0.25:1), pH 4.5 | 96.84% | 77.37% | 68.65% | 1.39% | |
| Formulation VIII | Saccharose + glycerol + tigecycline (2:0.15:1), pH 4.5 | 99.75% | 62.23% | 61.01% | 2.20% | The samples have shrunk into a mass after 10 days |
| Formulation IV | Mannitol + Vit C + glycerol + tigecycline (4:0.3:0.25:1), pH 4.5 | 96.23% | 62.72% | 59.64% | 1.59% | |
| Formulation IX | Mannitol + calcium chloride + tigecycline (4:0.4:1), pH 4.5 | — | — | — | 0.95% | Reconstituted is precipitated, without detection |

It can be seen from Table 1 that the formulation II (the advantageous formulation of patent CN 101132775 A) has optimal stability, and has remarkable advantages; meanwhile, related substances after 10 days at 60° C. still meet the specification; by comparing the purity of samples of formulations III, IV, VI and XI after 10 days at 60° C., it can be seen that the stability of the tigecycline becomes poor where Vitamin C, glycerol and Tween 80 are added; by comparing the purity of the freeze-dried samples of formuadjusted to 8.0 with 1 mol/l NaOH, and then the solution was distributed into 10 vials of 10 ml, with 2 ml per vial.

Formulation III: Vitamin C+tigecycline (0.5:1), pH 8.0

250 mg of Vitamin C was weighed and dissolved in 20 ml of deoxidized water, 500 mg of tigecycline was added and shaken for dissolution, the pH was adjusted to 8.0 with 1 mol/l NaOH, and then the solution was distributed into 10 vials of 10 ml, with 2 ml per vial.

Formulation IV: L-arginine+tigecycline (0.5:1), pH 8.0

250 mg of L-arginine was weighed and dissolved in 20 ml of deoxidized water, 500 mg of tigecycline was added and shaken for dissolution, the pH was adjusted to 8.0 with 1 mol/l HCl, and then the solution was distributed into 10 vials of 10 ml, with 2 ml per vial.

Formulation V: L-arginine+sodium chloride+tigecycline (0.5:0.4:1), pH 8.0

250 mg of L-arginine was weighed and dissolved in 20 ml of deoxidized water, and after 200 mg of sodium chloride was added and dissolved, 500 mg of tigecycline was added and shaken for dissolution, the pH was adjusted to 8.0 with 1 mol/l HCl, and then the solution was distributed into 10 vials of 10 ml, with 2 ml per vial.

Formulation VI: L-arginine+sodium sulfite+tigecycline (0.5:0.2:1), pH 8.0

250 mg of L-arginine was weighed and dissolved in 20 ml of deoxidized water, and after 100 mg of anhydrous sodium sulfite was added and dissolved, 500 mg of tigecycline was added and shaken for dissolution, the pH was adjusted to 8.0 with 1 mol/l HCl, and then the solution was distributed into 10 vials of 10 ml, with 2 ml per vial.

Formulation VIII: lactose+tigecycline (2:1), pH 4.5 (the advantageous formulation of patent CN 101132775 A)

1000 mg of lactose was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation IX: L-arginine+tigecycline (0.5:1), pH 4.5

250 mg of L-arginine was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

All the vials holding sample solutions were placed in the freeze dryer for freeze drying, and after freeze drying, the vials were charged with nitrogen, with compacted plugs and pressed caps. Moisture and purity were determined on day 0, then the remaining samples were placed in the drying oven at 60° C., and the purity was determined on day 5 and day 10. Experiment results are shown in Table 2 (data in the table is arranged from high to low for the purity on day 10 at 60° C.).

TABLE 2

| Formulation number | Formulation name | Purity at 60° C. on day 0 | Purity at 60° C. on day 5 | Purity at 60° C. on day 10 | Moisture % | Notes |
| --- | --- | --- | --- | --- | --- | --- |
| Formulation V | L-arginine + NaCl + tigecycline (0.5:0.4:1), pH 8.0 | 99.76% | 99.33% | 98.82% | 1.87% | The sample color has turned from orange yellow into grayish yellow after 10 days |
| Formulation VIII | lactose + tigecycline (2:1), pH 4.5 | 99.79% | 98.71% | 98.05% | 1.08% | |
| Formulation IX | L-arginine + tigecycline (0.5:1), pH 4.5 | 99.76% | 98.31% | 96.89% | 1.52% | |
| Formulation I | water + tigecycline, pH 8.0 | 99.31% | 98.15% | 96.67% | 1.35% | The sample color has turned from orange yellow into grayish yellow after 10 days |
| Formulation VI | L-arginine + sodium sulfite + tigecycline (0.5:0.2:1), pH 8.0 | 99.81% | 97.46% | 96.65% | 2.82% | The sample color has turned from orange yellow into grayish yellow after 10 days |
| Formulation IV | L-arginine + tigecycline (0.5:1), pH 8.0 | 99.68% | 98.34% | 96.41% | 1.17% | The sample color has turned from orange yellow into grayish yellow after 10 days |
| Formulation VII | L-arginine + Vitamin C + tigecycline (0.5:0.5:1), pH 8.0 | 99.05% | 96.40% | 95.27% | 4.20% | The sample color has turned from orange yellow into grayish yellow after 10 days |
| Formulation III | Vitamin C + tigecycline (0.5:1), pH 8.0 | 99.02% | 92.45% | 92.99% | 4.25% | The sample color has turned from orange yellow into grayish yellow after 10 days |
| Formulation II | sodium sulfite + tigecycline (0.2:1), pH 8.0 | 99.73% | 90.35% | 89.83% | 2.99% | The sample color has turned from orange yellow into grayish yellow after 10 days |

Formulation VII: L-arginine+Vitamin C+tigecycline (0.5:0.5:1), pH 8.0

250 mg of L-arginine was weighed and dissolved in 20 ml of deoxidized water, and after 250 mg of Vc was added and dissolved, 500 mg of tigecycline was added and shaken for dissolution, the pH was adjusted to 8.0 with 1 mol/l NaOH, and then the solution was distributed into 10 vials of 10 ml, with 2 ml per vial.

In Table 2, by comparing the purity of the freeze-dried samples of formulations V and VIII after 10 days at 60° C., although the purity of formulation V is higher than that of formulation VIII (the advantageous formulation of patent CN 101132775 A) after 10 days at 60° C., the color of the sample of formulation V changed after 10 days at 60° C., and moreover, the color of the upper layer solution of the reconstituted solution is found to have rapidly turned green from orange yellow during the purity determination; by comparing the purity of freeze-dried samples of formulations IV, VI and VII after 10 days at 60° C., it can be seen that the stability of tigecycline cannot be increased by selecting L-arginine and an antioxidant; by comparing the purity of freeze-dried samples of formulations IV and IX after 10 days at 60° C., it can be seen that the stability of the tigecycline can be increased by using L-arginine as the propping agent under acidic conditions.

In addition, L-arginine is a basic amino acid, and tigecycline can be easily oxidized under alkaline conditions; therefore, in order to reduce impurities generated during a preparation process, L-arginine is replaced with L-arginine hydrochloride.

EXAMPLE 3

Formulation I: water+tigecycline, pH 4.5

500 mg of tigecycline was weighed and dissolved in 20 ml of deoxidized water, the pH was adjusted to 4.5 with 1 mol/l HCl, and then the solution was distributed into 10 vials of 10 ml, with 2 ml per vial.

Formulation II: lactose+tigecycline (2:1), pH 4.5 (the advantageous formulation of patent CN 101132775 A)

1000 mg of lactose was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation III: threonine+tigecycline (2:1), pH 4.5 (the advantageous formulation of patent CN 102138925 A)

1000 mg of threonine was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation IV: L-arginine hydrochloride+tigecycline (0.61:1), pH 4.5

303 mg of L-arginine hydrochloride (containing 250 mg of L-arginine) was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation V: L-arginine hydrochloride+sodium chloride+tigecycline (0.61:0.4:1), pH 4.5

303 mg of L-arginine hydrochloride (containing 250 mg of L-arginine) was weighed and dissolved in 20 ml of deoxidized water, and after 200 mg of sodium chloride was added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation VI: L-arginine hydrochloride+sodium chloride+tigecycline (0.61:0.8:1), pH 4.5

303 mg of L-arginine hydrochloride (containing 250 mg of L-arginine) was weighed and dissolved in 20 ml of deoxidized water, and after 400 mg of sodium chloride was added and dissolved, 500 mg of tigecycline was added and shaken for dissolution, the pH was adjusted to 4.5 with 1 mol/l HCl, and then the solution was distributed into 10 vials of 10 ml, with 2 ml per vial.

Formulation VII: L-arginine hydrochloride+tigecycline (1.2:1), pH 4.5

606 mg of L-arginine hydrochloride (containing 500 mg of L-arginine) was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation VIII: L-arginine hydrochloride+tigecycline (2.4:1), pH 4.5

1212 mg of L-arginine hydrochloride (containing 1000 mg of L-arginine) was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation IX: L-arginine hydrochloride+tigecycline (0.3:1), pH 4.5

152 mg of L-arginine hydrochloride (containing 125 mg of L-arginine) was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation X: L-arginine hydrochloride+tigecycline (0.61:1), pH 6.0

303 mg of L-arginine hydrochloride (containing 250 mg of L-arginine) was weighed and dissolved in 20 ml of deoxidized water, 500 mg of tigecycline was added and shaken for dissolution, the pH was adjusted to 6.0 with 1 mol/l HCl, and then the solution was distributed into 10 vials of 10 ml, with 2 ml per vial.

Formulation XI: dextran-20+sodium sulfite+sodium citrate+tigecycline (2:0.1:0.1:1), pH 8.0 (the advantageous formulation of patent CN 101401812 B)

1000 mg of dextran-20 was weighed and dissolved in 20 ml of deoxidized water, and after 50 mg of anhydrous sodium sulfite and 50 mg of sodium citrate were added and dissolved, 500 mg of tigecycline was added and shaken for dissolution, the pH was adjusted to 8.0 with 1 mol/l HCl, and then the solution was distributed into 10 vials of 10 ml, with 2 ml per vial.

All the vials holding sample solutions were placed in the freeze dryer for freeze drying, and after freeze drying, the vials were charged with nitrogen, capped with a rubber stopper and a seal. Moisture and purity were determined at day 0; two vials of samples of each formulation were taken and placed in the drying oven at 60° C., and the purity was determined on day 5 and day 10; two vials of samples of each formulation were taken and placed in a constant temperature humidity chamber of 40° C./75% RH, and the advantageous formulation and the formulations in the patents were selected for purity determination on day 68. Experiment results are shown in Table 3a (data in the table is arranged from high to low for the purity on day 10 at 60° C.).

Moreover, one vial of each freeze-dried sample of formulations II, V, VII, VIII and XI which was placed at 60° C. for 5 days was taken, 5 ml of normal saline was added and shaken for dissolution, and the reconstituted solution was left at 25° C./60% RH for 6 hours and the purity was determined, in order to mimically survey the stability of a commercially available product reconstituted solution. After the reconstituted solution was left for 6 hours, 45 ml of normal saline was added for dilution, the diluted solution was placed at 25° C./60% RH for 18 hours and the purity was determined, in order to mimically survey the stability of a commercially available product diluted solution. Experiment results are shown in Table 3b.

TABLE 3a

| Formulation number | Formulation name (weight ratio) | Purity at 60° C. on day 0 | Purity at 60° C. on day 5 | Purity at 60° C. on day 10 | Purity at 40° C./75% RH on day 68 | Moisture % | Notes |
|---|---|---|---|---|---|---|---|
| Formulation V | L-arginine hydrochloride + NaCl + tigecycline (0.61:0.4:1), pH 4.5 | 99.88% | 99.57% | 99.51% | 99.17% | 1.48% | |
| Formulation VII | L-arginine hydrochloride + tigecycline (1.2:1), pH 4.5 | 99.83% | 99.31% | 99.04% | | 1.89% | |
| Formulation VI | L-arginine hydrochloride + NaCl + tigecycline (0.61:0.8:1), pH 4.5 | 99.79% | 99.41% | 99.03% | | 1.30% | |
| Formulation VIII | L-arginine hydrochloride + tigecycline (2.4:1), pH 4.5 | 99.81% | 99.72% | 98.83% | | 2.69% | |
| Formulation II | lactose + tigecycline (2:1), pH 4.5 | 99.81% | 98.75% | 98.65% | 97.93% | 1.68% | Patent CN101132775A advantageous formulation |
| Formulation XI | dextran + sodium sulfite + sodium citrate + tigecycline (2.0:0.1:0.1:1), pH 8.0 | 99.87% | 99.20% | 98.42% | 97.83% | 2.23% | Patent CN101401812B advantageous formulation, 60° C. for 10 days, 40° C./75% RH, the sample color has turned from orange yellow into grayish yellow on day 68 |
| Formulation IV | L-arginine hydrochloride + tigecycline (0.61:1), pH 4.5 | 99.78% | 98.59% | 98.27% | | 2.03% | |
| Formulation X | L-arginine hydrochloride + tigecycline (0.61:1), pH 6.0 | 99.90% | 98.83% | 98.03% | | 2.41% | |
| Formulation IX | L-arginine hydrochloride + tigecycline (0.3:1), pH 4.5 | 99.84% | 96.50% | 94.46% | | 2.20% | |
| Formulation I | water + tigecycline, pH 4.5 | 99.74% | 94.25% | 93.68% | | 2.42% | |
| Formulation III | threonine + tigecycline (2:1), pH 4.5 | 99.75% | 75.92% | 66.84% | 88.72% | 3.87% | Patent CN102138925A, advantageous formulation |

TABLE 3b

| Formulation number | Formulation name (weight ratio) | Purity of reconstituted solution at 0 h | Purity of reconstituted solution, at 25° C., at 6 h | Purity of diluted solution, at 25° C., at 18 h |
|---|---|---|---|---|
| Formulation V | L-arginine hydrochloride + NaCl + tigecycline (0.61:0.4:1), pH 4.5 | 99.68% | 98.92% | 98.85% |
| Formulation VIII | L-arginine hydrochloride + tigecycline (2.4:1), pH 4.5 | 99.66% | 99.08% | 98.81% |
| Formulation VII | L-arginine hydrochloride + tigecycline (1.2:1), pH 4.5 | 99.15% | 98.48% | 98.21% |
| Formulation XI | dextran + sodium sulfite + sodium citrate + tigecycline (2:0.1:0.1:1), pH 8.0 | 99.28% | 98.39% | 97.69% |
| Formulation II | lactose + tigecycline (2:1), pH 4.5 | 98.70% | 97.56% | 97.49% |

In Table 3a, by comparing the purity of freeze-dried samples of formulations IV, VII, VIII and IX on day 10 at 60° C., it can be seen that along with the increase of the amount of L-arginine hydrochloride within a certain range in the composition, the stability of tigecycline is also increased; by comparing the purity of freeze-dried samples of formulations IV, V and VI on day 10 at 60° C., it can be seen that tigecycline can be made more stable by adding a proper amount of sodium chloride; by comparing the purity of freeze-dried samples of formulations IV and X on day 10 at 60° C., it can be seen that tigecycline is stable between pH 4.5 and 6; the sample of formulation XI is relatively stable, the sample appearance of the freeze-dried sample of this formulation has changed after 10 days at 60° C., and moreover, the sample dissolves at a low rate and foam is easily generated by shaking; and it can be seen from Tables 3a and 3b, whether it is the freeze-dried sample or the sample reconstituted solution and diluted solution, the prescription of L-arginine hydrochloride+NaCl+tigecycline (0.61:0.4:1), pH 4.5 is superior to the formulation (the advantageous formulation of patent CN101132775 A) lactose+tigecycline (2:1), pH 4.5 in stability.

EXAMPLE 4

Formulation I: lactose+tigecycline (2:1), pH 4.5 (the advantageous formulation of patent CN101132775 A)

1000 mg of lactose was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation II: L-arginine hydrochloride+sodium chloride+tigecycline (0.61:0.4:1), pH 4.5

303 mg of L-arginine hydrochloride (containing 250 mg of L-arginine) was weighed and dissolved in 20 ml of deoxidized water, and after 200 mg of sodium chloride was added and dissolved, 500 mg of tigecycline was added and shaken for dissolution, the pH was adjusted to 4.5 with 1 mol/l HCl, and then the solution was distributed into 10 vials of 10 ml, with 2 ml pervial.

Formulation III: D-arginine+tigecycline (2:1), pH 4.5

1000 mg of D-arginine was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation IV: DL-arginine+tigecycline (2:1), pH 4.5

1000 mg of DL-arginine was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

Formulation V: serine+tigecycline (2:1), pH 4.5 (the advantageous formulation of patent CN 102138925 A)

1000 mg of threonine was weighed and dissolved in 20 ml of deoxidized water, 500 mg of tigecycline was added and shaken for dissolution, the pH was adjusted to 4.5 with 1 mol/1 HCl, and then the solution was distributed into 10 vials of 10 ml, with 2 ml per vial.

Formulation VI: methionine+tigecycline (1:1), pH 4.5 (patent CN 101152152 A relates to the methionine)

500 mg of methionine was weighed and dissolved in 20 ml of deoxidized water, 500 mg of tigecycline was added and shaken for dissolution, the pH was adjusted to 4.5 with 1 mol/l HCl, and then the solution was distributed into 10 vials of 10 ml, with 2 ml per vial.

All the vials holding sample solutions were placed in the freeze dryer for freeze drying, and after freeze drying, the bottles were charged with nitrogen, with compacted plugs and pressed caps. Moisture and purity were determined on day 0, then the remaining samples were placed in the drying oven at 60° C., and the purity was determined on day 10. Experiment results are shown in Table 4a (data in the table is arranged from high to low for the purity on day 10 at 60° C.).

Furthermore, one vial of each sample of formulations I and II which was placed at 60° C. for 10 days was taken, 5 ml of 5% glucose solution was respectively added and shaken for dissolution, and the reconstituted solution was left at 25° C./60% RH for 6 hours, and the purity was determined at hour 0 and hour 6. Six hours later, 45 ml of 5% glucose solution was respectively added for dilution, and the diluted solution was left at 25° C./60% RH for 18 hours, and then the purity was determined. Experiment results are shown in Table 4b.

Furthermore, one vial of each sample of formulations I and II which was left at 60° C. for 10 days was taken, 5 ml of lactated Ringer's solution was added and shaken for dissolution, and the reconstituted solution was placed at 25° C./60% RH for 6 hours, and the purity was determined at hour 0 and hour 6. Six hours later, lactated Ringer's solution was respectively added for dilution, and the diluted solution was placed at 25° C./60% RH for 18 hours, and then determined for the purity. Experiment results are shown in Table 4c.

TABLE 4a

| Formulation number | Formulation name (weight ratio) | 60° C. purity on day 0 | 60° C. purity on day 10 | Moisture % | Notes |
|---|---|---|---|---|---|
| Formulation III | D-arginine + tigecycline (2:1), pH 4.5 | 99.69% | 98.90% | 2.15% | |
| Formulation II | L-arginine hydrochloride + NaCl + tigeCycline (0.61:0.4:1), pH 4.5 | 99.73% | 98.58% | 3.71% | |
| Formulation IV | DL-arginine + tigecycline (0:1), pH 4.5 | 99.35% | 98.55% | 2.83% | |
| Formulation I | lactose + tigecycline (2:1), pH 4.5 | 99.72% | 97.84% | 0.95% | Patent CN101132775 A, advantageous formulation |
| Formulation VI | L-methionine + tigecycline (1:1), pH 4.5 | 99.58% | 92.05% | 3.01% | Patent CN101152152 A relates to methionine |
| Formulation V | L-serine + tigecycline (2:1), pH 4.5 | 99.66% | 80.26% | 3.31% | Patent CN 102138925 A, advantageous formulation |

TABLE 4b

| Formulation number | Formulation name (weight ratio) | Purity of reconstituted solution, at 25° C., at 0 h | Purity of reconstituted solution, at 25° C., at 6 h | Purity of diluted solution, at 25° C., at 18 h |
|---|---|---|---|---|
| Formulation I | lactose + tigecycline (2:1), pH 4.5 | 97.88% | 97.40% | 96.41% |
| Formulation II | L-arginine hydrochloride + NaCl + tigecycline (0.61:0.4:1), pH 4.5 | 98.74% | 97.95% | 96.89% |

TABLE 4c

| Formulation number | Formulation name (weight ratio) | Purity of reconstituted solution, at 25° C., at 0 h | Purity of reconstituted solution, at 25° C., at 6 h | Purity of diluted solution, at 25° C., at 18 h |
|---|---|---|---|---|
| Formulation I | lactose + tigecycline (2:1), pH 4.5 | 97.85% | 96.82% | 95.51% |
| Formulation II | L-arginine hydrochloride + NaCl + tigecycline (0.61:0.4:1), pH 4.5 | 97.92% | 97.05% | 95.85% |

It can be seen from the results in Table 4a that the stability of tigecycline can be increased by D-arginine and DL-arginine as well; it can be seen from Table 4b that the samples of formulation I are superior to the samples of formulation II in the stability of the reconstituted solution within 6 hours and the diluted solution within 18 h using 5% glucose solution; and it can be seen from Table 4c that the samples of formulation II are superior to the samples of formulation I in the stability of the reconstituted solution within 6 hours and the diluted solution within 18 h using lactated Ringer's solution.

The invention claimed is:

1. A freeze-dried tigecycline composition for injection, comprising:
   tigecycline;
   a propping agent;
   a pH adjuster; and
   optionally a stabilizing agent;
   wherein said propping agent is selected from one or several of L-arginine, L-arginine hydrochloride, and a salt formed by L-arginine with acid or alkali;
   wherein the weight ratio among components of the tigecycline composition for injection is: tigecycline 1.0, the propping agent 0.3-4, and the stabilizing agent 0-2;
   wherein the pH adjuster is present in an amount to provide a pH of 4.0-6.0 of a solution comprised of the tigecycline composition for injection prior to freeze drying; and
   wherein each of tigecycline, the propping agent, the pH adjuster, and optionally, the stabilizing agent, is present as a freeze-dried solid.

2. The freeze-dried tigecycline composition for injection as claimed in claim 1, wherein said propping agent is L-arginine or L-arginine hydrochloride.

3. The freeze-dried tigecycline composition for injection as claimed in claim 1, wherein said stabilizing agent is sodium chloride.

4. The freeze-dried tigecycline composition for injection as claimed in claim 1, wherein said pH adjuster is hydrochloric acid, sodium hydroxide or a mixture thereof.

5. The freeze-dried tigecycline composition for injection as claimed in claim 1, wherein the amount of tigecycline is 50 mg.

6. A pharmaceutical composition comprised of the freeze-dried tigecycline composition for injection as claimed in claim 1 reconstituted with a suitable amount of a pharmaceutically acceptable diluent.

7. The pharmaceutical composition as claimed in claim 6, wherein said diluent is normal saline, 5% glucose solution or lactated Ringer's solution.

8. A stable and pharmaceutically acceptable reconstituted solution of freeze-dried tigecycline, wherein it is prepared by treating the freeze-dried powder of the tigecycline composition for injection as claimed in claim 1 with a suitable amount of a pharmaceutically acceptable diluent.

9. The reconstituted solution as claimed in claim 8, wherein said diluent is normal saline, 5% glucose solution or lactated Ringer's solution.

10. The freeze-dried tigecycline composition for injection of claim 1, wherein the propping agent is L-arginine; wherein weight ratio among components of the tigecycline composition for injection is: tigecycline 1.0, L-arginine 0.5; and wherein the solution comprised of the tigecycline composition for injection prior to freeze drying has a pH of 4.5.

11. The freeze-dried tigecycline composition for injection of claim 1, wherein the propping agent is L-arginine hydrochloride; wherein the weight ratio among components of the tigecycline composition for injection is: tigecycline 1.0, L-arginine hydrochloride 0.61; and wherein the solution comprised of the tigecycline composition for injection prior to freeze drying has a pH of 4.5.

12. The freeze-dried tigecycline composition for injection of claim 1, wherein the propping agent is L-arginine hydrochloride; wherein the weight ratio among components of the tigecycline composition for injection is: tigecycline 1.0, L-arginine hydrochloride 1.2; and wherein the solution comprised of the tigecycline composition for injection prior to freeze drying has a pH of 4.5.

13. The freeze-dried tigecycline composition for injection of claim 1, wherein the propping agent is L-arginine hydrochloride; wherein the weight ratio among components of the tigecycline composition for injection is: tigecycline 1.0, L-arginine hydrochloride 2.4; and wherein the solution comprised of the tigecycline composition for injection prior to freeze drying has a pH of 4.5.

14. The freeze-dried tigecycline composition for injection of claim 1, wherein the propping agent is L-arginine hydrochloride; wherein the weight ratio among components of the tigecycline composition for injection is: tigecycline 1.0, L-arginine hydrochloride 0.3; and wherein the solution comprised of the tigecycline composition for injection prior to freeze drying has a pH of 4.5.

15. The freeze-dried tigecycline composition for injection of claim 1, wherein the weight ratio among components of the tigecycline composition for injection is: tigecycline 1.0, propping agent 0.61-2.4.

16. The freeze-dried tigecycline composition for injection as claimed in claim 15, wherein the amount of tigecycline is 50 mg.

17. The freeze-dried tigecycline composition for injection of claim 1, wherein the weight ratio among components of the tigecycline composition for injection is: tigecycline 1.0, propping agent 1.2-2.4.

18. The freeze-dried tigecycline composition for injection as claimed in claim 17, wherein the amount of tigecycline is 50 mg.

19. The freeze-dried tigecycline composition for injection as claimed in claim 17, wherein said propping agent is L-arginine.

20. The freeze-dried tigecycline composition for injection as claimed in claim 17, wherein said propping agent is L-arginine hydrochloride.

21. The freeze-dried tigecycline composition for injection as claimed in claim 17, wherein said propping agent is a salt formed by L-arginine with acid or alkali.

* * * * *